United States Patent
Si et al.

(10) Patent No.: US 10,575,820 B2
(45) Date of Patent: Mar. 3, 2020

(54) ULTRASONIC TRANSDUCER

(71) Applicant: SHENZHEN MINDRAY BIO-MEDICAL ELECTRONICS CO., LTD., Shenzhen (CN)

(72) Inventors: Kang Si, Shenzhen (CN); Fei Wu, Shenzhen (CN); Zhenyu Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 15/890,744

(22) Filed: Feb. 7, 2018

(65) Prior Publication Data
US 2018/0161006 A1 Jun. 14, 2018

Related U.S. Application Data

(63) Continuation of application No. PCT/CN2015/087981, filed on Aug. 25, 2015.

(51) Int. Cl.
*A61B 8/00* (2006.01)
*B06B 1/06* (2006.01)

(52) U.S. Cl.
CPC .......... *A61B 8/4483* (2013.01); *A61B 8/4281* (2013.01); *A61B 8/4444* (2013.01); *A61B 8/4494* (2013.01); *B06B 1/0607* (2013.01); *B06B 1/0622* (2013.01)

(58) Field of Classification Search
CPC ... A61B 8/4483; A61B 8/4281; A61B 8/4444; A61B 8/4494; B06B 1/0622
See application file for complete search history.

(56) References Cited

U.S. PATENT DOCUMENTS

| 5,212,671 A | 5/1993 | Fujii et al. |
| 5,409,411 A | 4/1995 | Schrieber |
| 5,423,220 A * | 6/1995 | Finsterwald .......... B06B 1/0622 310/322 |
| 5,438,998 A * | 8/1995 | Hanafy ................. B06B 1/0622 310/334 |
| 9,452,447 B2 * | 9/2016 | Zhao ..................... B06B 1/0622 |
| 9,808,830 B2 * | 11/2017 | Tai ....................... G01S 7/52017 |
| 2003/0189391 A1 * | 10/2003 | Shimizu ................ B06B 1/0622 310/334 |
| 2006/0142659 A1 * | 6/2006 | Okazaki ................ B06B 1/0622 600/459 |
| 2007/0189761 A1 * | 8/2007 | Sudol ..................... A61B 8/4483 396/316 |

(Continued)

FOREIGN PATENT DOCUMENTS

| CN | 1741770 A | 3/2006 |
| CN | 101273382 A | 9/2008 |

(Continued)

*Primary Examiner* — J. San Martin
(74) *Attorney, Agent, or Firm* — Kory D. Christensen

(57) ABSTRACT

An ultrasonic transducer may include a piezoelectric wafer and backing layers. The backing layers may include a high impedance backing layer and a low impedance backing layer. The back surface of the piezoelectric wafer may be connected with the front surface of the high impedance backing layer, and the back surface of the high impedance backing layer may be connected with the front surface of the low impedance backing layer.

18 Claims, 7 Drawing Sheets

(56) References Cited

U.S. PATENT DOCUMENTS

| | | | |
|---|---|---|---|
| 2009/0069689 A1* | 3/2009 | Isono | B06B 1/0622 600/459 |
| 2009/0069691 A1* | 3/2009 | Saito | B60B 1/0622 600/459 |
| 2009/0072668 A1* | 3/2009 | Gelly | G10K 11/02 310/334 |
| 2012/0056512 A1* | 3/2012 | Jin | A61B 8/00 310/335 |
| 2014/0082907 A1* | 3/2014 | Barthe | B06B 1/0622 29/25.35 |
| 2014/0290371 A1* | 10/2014 | Nakamura | G01N 29/28 73/644 |
| 2015/0183000 A1 | 7/2015 | Tai et al. | |
| 2016/0213350 A1* | 7/2016 | Lee | A61B 8/429 |

FOREIGN PATENT DOCUMENTS

| | | |
|---|---|---|
| CN | 103300893 | 9/2013 |
| CN | 103512649 A | 1/2014 |

\* cited by examiner

ULTRASONIC TRANSDUCER

CROSS-REFERENCE TO RELATED APPLICATIONS

This application is a continuation of Patent Cooperation Treaty Application No. PCT/CN2015/087981, filed Aug. 25, 2015, for "Ultrasonic Transducer," which is incorporated herein by reference.

TECHNICAL FIELD

The present disclosure relates to ultrasonic imaging and more particularly to an ultrasonic transducer.

BACKGROUND

In an ultrasonic diagnostic device, ultrasonic transducers convert electrical signals into ultrasonic waves that propagate in human tissue and convert the ultrasonic waves reflected back by the human tissue into electrical signals. The electrical signals can be processed and displayed on a display device as images for analysis and disease diagnosis by s doctor.

Bandwidth is an important characteristic for measuring the quality of an ultrasonic transducer. Wideband ultrasonic transducers can transmit and receive ultrasonic waves with different frequencies so as to satisfy different requirements, such as when the diagnostic device uses different operating frequencies in near field and far field. Furthermore, a wideband ultrasonic transducer can be used in harmonic imaging. With a wide frequency band, the multiple harmonics of sound waves generated in human tissues can be received, and thereby the axial resolution and sensitivity of the images can be increased.

SUMMARY

An ultrasonic transducer and an ultrasonic diagnostic device using the same are disclosed herein.

DETAILED DESCRIPTION

Figure 1:
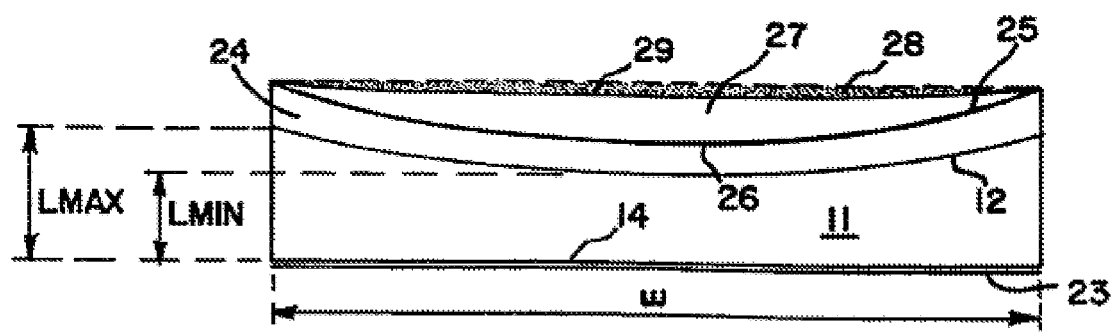
FIG. 1 schematically shows a first existing ultrasonic transducer.

A wideband ultrasonic transducer is shown in FIG. 1, where the thicker the piezoelectric crystal 11 is, the lower the operating frequency of the corresponding transducer may be. By adjusting the maximum thickness LMAX and the minimum thickness LMIN of the piezoelectric crystal, the transducer may have good sensitivity from low to high frequency, thereby broadening the bandwidth. However, the range of the bandwidth broadened by this technique is limited. Restricted by the manufacturing processes, the value of LMAX/LMIN is generally less than or equal to 140% (LMAX/LMIN≤140%). If this value is too large, the piezoelectric crystal is prone to be broken when manufacturing the transducer.

Figure 2:
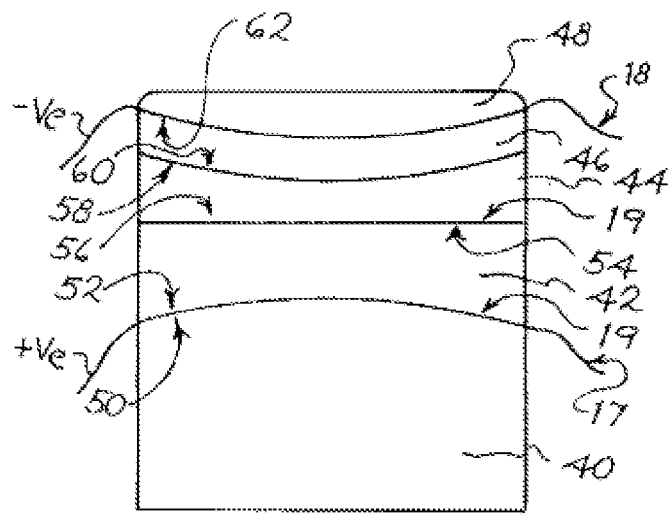
FIG. 2 schematically shows a second existing ultrasonic transducer.
Figure 3:
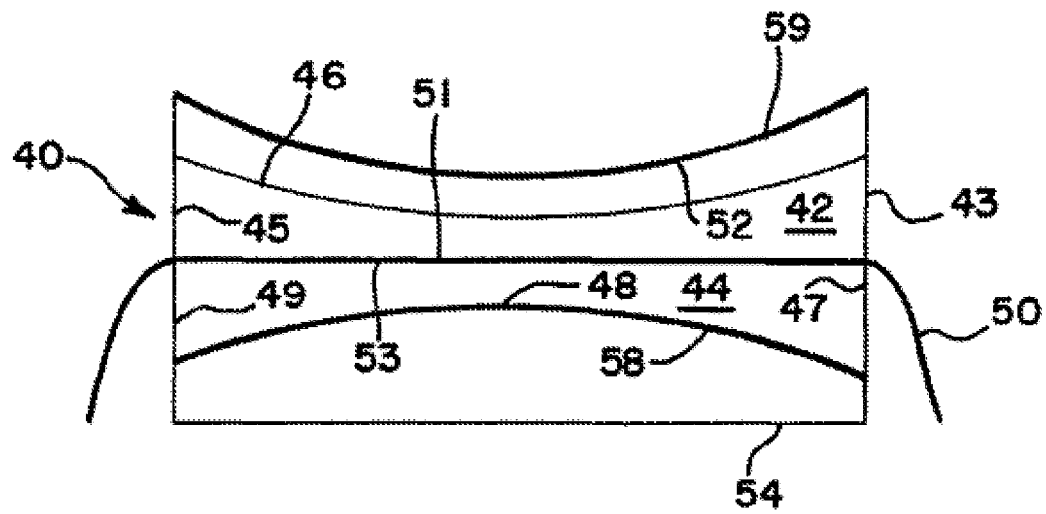
FIG. 3 schematically shows a third existing ultrasonic transducer.
Figure 4:
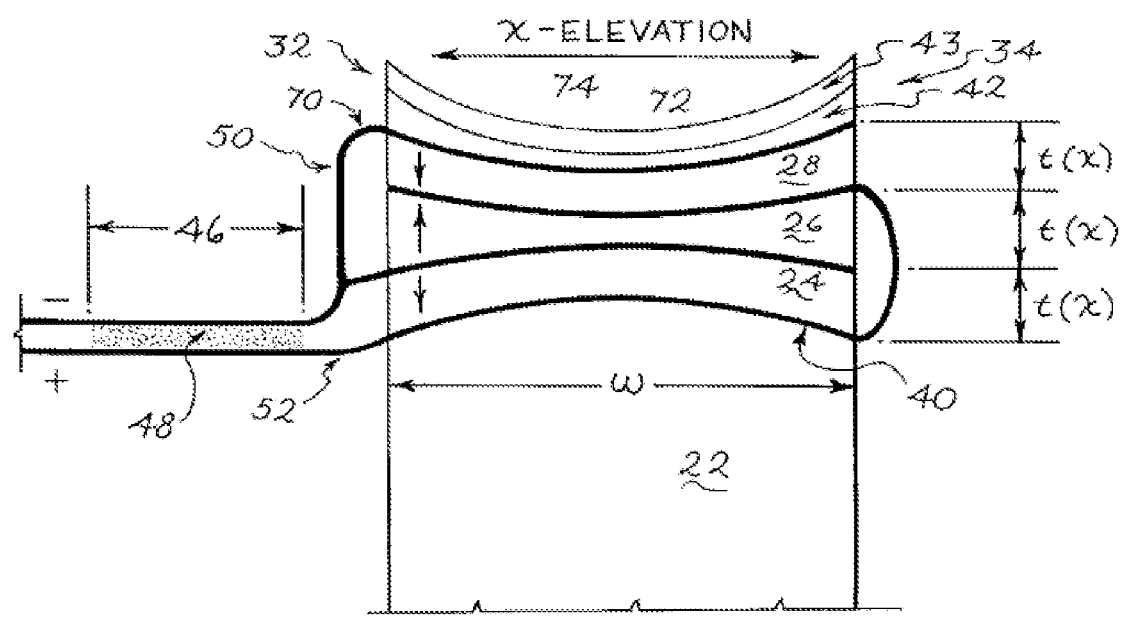
FIG. 4 schematically shows a fourth existing ultrasonic transducer.

Another wideband ultrasonic transducer is shown in FIG. 2, where the concave surface of the piezoelectric crystal 42 is connected with the backing layer 40, thereby reducing the possibility of cracking of the piezoelectric crystal during pressure bonding. In other solutions, the transducer may include two layers of piezoelectric crystal 42, 44 with non-constant thicknesses, as shown in FIG. 3. Alternatively, the transducer may include three layers of piezoelectric crystal 24, 26 and 28 with non-constant thicknesses, as shown in FIG. 4. Such solutions with multiple layers of piezoelectric crystal with non-constant thicknesses may reduce the curvatures of the upper surface and the lower surface under the condition that the total equivalent curvature is guaranteed, thereby reducing the possibility of cracking of the piezoelectric crystals. However, in these solutions, the piezoelectric crystals prone to be broken are formed as concave shapes with non-constant thicknesses, which increases the manufacturing difficulty, thereby the possibility of cracking of the piezoelectric crystal still existing. Furthermore, since the piezoelectric crystals are concave, the difficulty of forming the covering electrode on the piezoelectric crystals is increased.

In one embodiment, an ultrasonic transducer may be provided, which may include a piezoelectric crystal and a backing layer. The backing layer may include a high impedance backing layer and a low impedance backing layer. The back surface of the piezoelectric crystal may be connected with the front surface of the high impedance backing layer, and the back surface of the high impedance backing layer may be connected with the front surface of the low impedance backing layer. The high impedance backing layer may have non-constant thicknesses.

In one embodiment, the piezoelectric crystal may have a constant thickness.

In one embodiment, the thickness at the middle of the high impedance backing layer may be smaller than the thicknesses at both sides of the high impedance backing layer.

In one embodiment, the back surface of the high impedance backing layer may be a curved concave surface, a wedge-shaped concave surface or a trapezoidal concave surface.

In one embodiment, both the piezoelectric crystal and the high impedance backing layer may have non-constant thicknesses.

In one embodiment, the thickness at the middle of the piezoelectric crystal may be smaller than the thicknesses at both sides of the piezoelectric crystal, and the thickness at the middle of the high impedance backing layer may be smaller than thicknesses at both sides of the high impedance backing layer.

In one embodiment, the front surface of the piezoelectric crystal may be a concave surface, the back surface of the piezoelectric crystal may be a flat surface, the front surface of the high impedance backing layer may be a flat surface, and the back surface of the high impedance backing layer may be a curved concave surface, a wedge-shaped concave surface or a trapezoidal concave surface.

In one embodiment, the piezoelectric crystal may have a constant thickness. The thickness at middle of the high impedance backing layer may be smaller than thicknesses at both sides of the high impedance backing layer and the back surface of the high impedance backing layer may be a concave surface. The thickness at the middle of the low impedance backing layer may be larger than the thicknesses at both sides of the low impedance backing layer and the front surface of the low impedance backing layer may be a convex surface. The back surface of the high impedance backing layer may match with the front surface of the low impedance backing layer.

In one embodiment, the ultrasonic transducer may further include a matching layer. The back surface of the matching layer may be connected with the front surface of the piezoelectric crystal. The matching layer may have a non-constant or constant thickness.

The element, such as the matching layer, the piezoelectric crystal, the high impedance backing layer, or the low impedance backing layer, may have maximum thickness and minimum thickness. In one embodiment, the element with constant thickness may refer to the element whose maximum and minimum thicknesses are equal, and the element with non-constant thickness may refer to that the element whose maximum and minimum thicknesses are different.

In one embodiment, an ultrasonic diagnostic device may be provided. The ultrasonic diagnostic device may include a piezoelectric crystal and a backing layer. The backing layer may include a high impedance backing layer and a low impedance backing layer. The back surface of the piezoelectric crystal may be connected with the front surface of the high impedance backing layer, and the back surface of the high impedance backing layer may be connected with the front surface of the low impedance backing layer. The high impedance backing layer may have non-constant thicknesses.

In various embodiments, the backing layer may include a high impedance backing layer and a low impedance backing layer and strong reflection may occur at the interface therebetween, such that more sound waves can be reflected back to the piezoelectric crystal, thereby increasing the sensitivity of the ultrasonic transducer. Furthermore, the piezoelectric crystal with constant thickness and the high impedance backing layer with non-constant thicknesses may be used to replace the piezoelectric crystal with non-constant thicknesses, thereby reducing the difficulty in manufacturing the piezoelectric crystal and effectively reducing the risk of cracking of the piezoelectric crystal.

Figure 5:
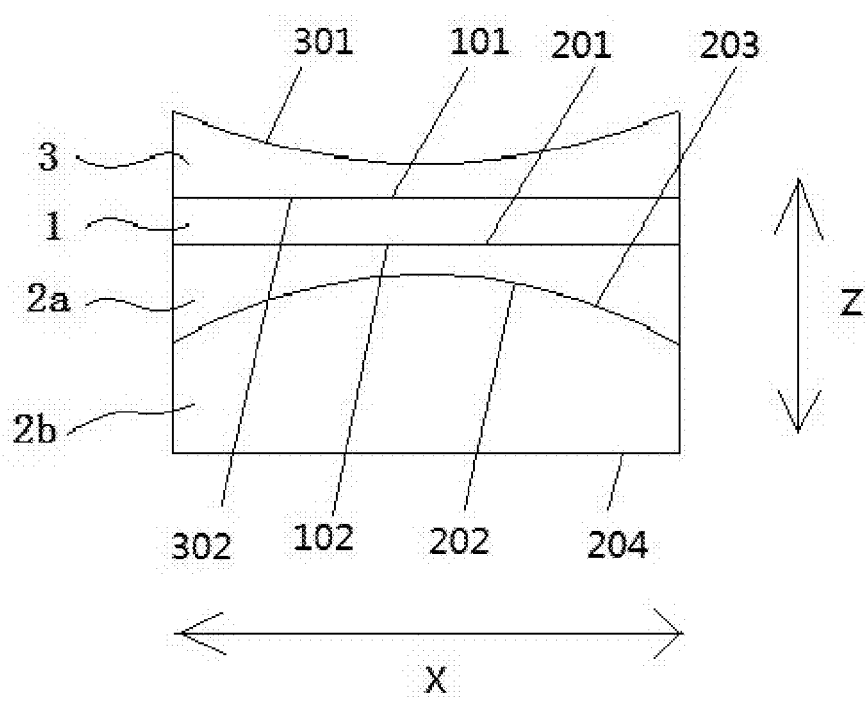
FIG. 5 schematically shows one embodiment of the ultrasonic transducer.

As shown in FIG. 5, an ultrasonic transducer may include a matching layer 3, a piezoelectric crystal 1, a high impedance backing layer 2a and a low impedance backing layer 2b. The matching layer, the piezoelectric crystal, the high impedance backing layer and the low impedance backing layer may be sequentially stacked from top to bottom. The piezoelectric crystal may be a piezoelectric crystal with a constant thickness. The high impedance backing layer may be a high impedance backing layer with non-constant thickness, back surface of the piezoelectric crystal may be connected with front surface of the high impedance backing layer thereby forming an equivalent piezoelectric crystal which is able to be equivalent to the piezoelectric crystal with non-constant thickness.

In the present disclosure, the "high impedance backing layer" may be a backing layer with relatively (e.g., with respect to the low impedance backing layer) high acoustic impedance. For example, the high impedance backing layer may be formed using backing materials with relatively (e.g., with respect to the materials of the low impedance backing layer) high acoustic impedance. Similarly, the "low impedance backing layer" may be a backing layer with relatively (e.g., with respect to the high impedance backing layer) low acoustic impedance. For example, the low impedance backing layer may be formed using backing materials with relatively (e.g., with respect to the materials of the high impedance backing layer) low acoustic impedance.

The principles of the equivalent piezoelectric crystal will be briefly described below.

Figure 6:
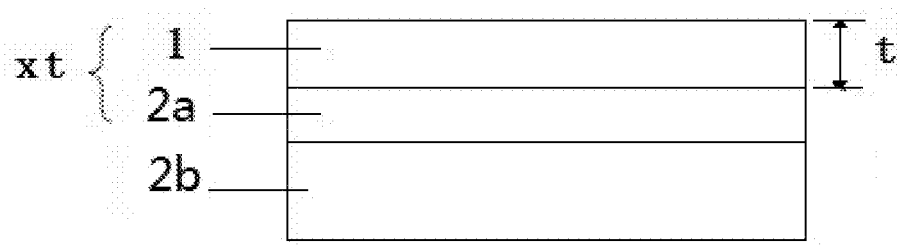
FIG. 6 is a schematic diagram which shows how a high impedance backing layer and the piezoelectric crystal with constant thickness are equivalent to a piezoelectric crystal with non-constant thickness.

As shown in FIG. 6, 1 represents the piezoelectric crystal, 2a represents the high impedance backing layer, and 2b represents the low impedance backing layer. When the piezoelectric crystal 1 operates and transmits ultrasonic waves, most of the ultrasonic waves propagating backwards will enter into the high impedance backing layer 2a and be relatively strongly reflected by the interface between the high impedance backing layer 2a and the low impedance backing layer 2b. The reflected ultrasonic waves will pass through the piezoelectric crystal 1 and propagate forwards. This way, the piezoelectric crystal 1 and the high impedance backing layer 2a may form an equivalent vibrator (i.e., an equivalent piezoelectric crystal), where the resonant frequency of the equivalent vibrator is inversely proportional to the thickness of the high impedance backing layer 2a. Therefore, the vibration frequency, i.e., the operation frequency, of the equivalent vibrator may be changed by changing the thickness of the high impedance backing layer 2a, thereby broadening the bandwidth of the ultrasonic transducer.

In the present disclosure, a single element (such as the matching layer, the piezoelectric crystal, the high impedance backing layer or the low impedance backing layer) may have a maximum thickness and a minimum thickness. A single element "with constant thickness" may refer to that the maximum and minimum thicknesses of the single element are equal. A single element "with non-constant thickness" may refer to that the maximum and minimum thicknesses of the single element are different.

Figure 14:
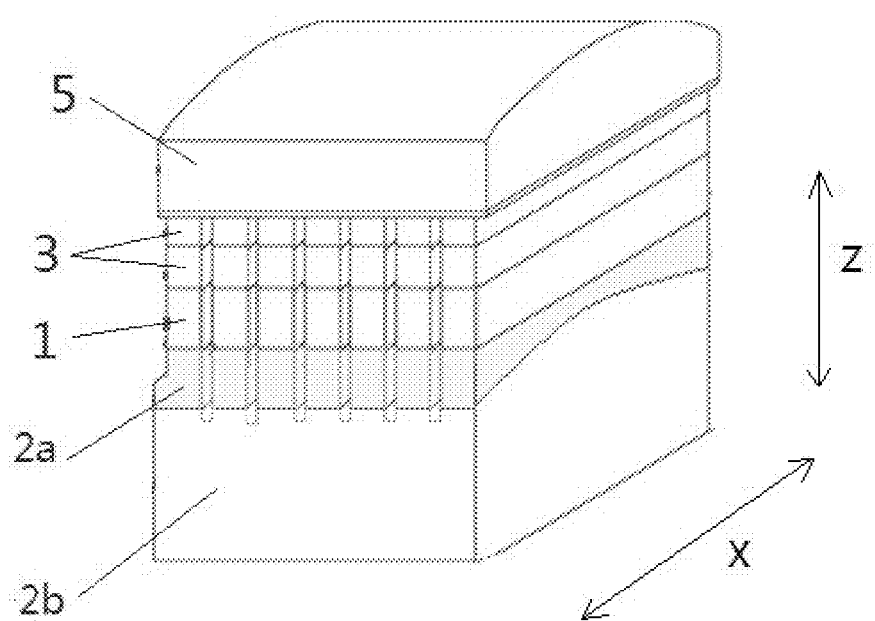
FIG. 14 is a perspective view of the ultrasonic transducer.

As shown in FIG. 5 and FIG. 14, the ultrasonic transducer may include a matching layer 3, a piezoelectric crystal 1, a high impedance backing layer 2a and a low impedance backing layer 2b. The back surface 302 of the matching layer 3 may be connected with the front surface 101 of the piezoelectric crystal 1. The back surface 102 of the piezoelectric crystal 1 may be connected with the front surface 201 of the high impedance backing layer 2a. The back surface 202 of the high impedance backing layer 2a may be connected with the front surface 203 of the low impedance backing layer 2b. The piezoelectric crystal 1 may have a constant thickness t. The front surface 101 and the back surface 102 of the piezoelectric crystal 1 may both be flat surface. The high impedance backing layer 2a may have non-constant thicknesses (e.g., the thicknesses in the Z direction are varying along the X direction in FIG. 5, but not constant). The thicknesses at the middle of the high impedance backing layer 2a may be smaller than those at both sides. The front surface 201 of the high impedance backing layer 2a may be a flat surface while the back surface 202 may be a curved concave surface. The low impedance backing layer 2b may have non-constant thicknesses. The thicknesses at the middle of the low impedance backing layer 2b may be larger than those at both sides. The front surface 203 of the low impedance backing layer 2b may be a curved convex surface matching with the back surface of the high impedance backing layer. The matching layer 3 may have non-constant thicknesses. The front surface 301 of the matching layer 3 may be a concave surface and the back surface 302 may be a flat surface. The back surface 204 of the low impedance backing layer 2b may be a flat surface. The front surface 301 of the matching layer may be connected with an acoustic lens 5.

As shown in FIG. 5, the left and right direction X may be perpendicular to the front and back direction Z, the "thickness", for a single element (such as the matching layer, the piezoelectric crystal, the high impedance backing layer or the low impedance backing layer), may refer to the difference between the Z coordinates at the front surface and the back surface which have the same X coordinate, and the "middle" and the "both sides" may refer to the middle and both sides in the left and right direction X.

Figure 7:
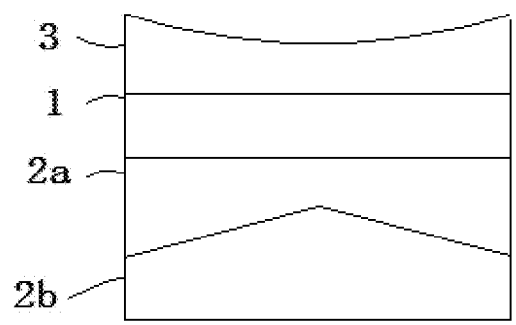
FIG. 7 schematically shows one embodiment of the ultrasonic transducer.

Referring to FIG. 7, an ultrasonic transducer is shown in which the back surface of the high impedance backing layer 2a may be a wedge-shaped concave surface, the wedge tip of the wedge-shaped concave surface may point to the piezoelectric crystal, and, correspondingly, the front surface of the low impedance backing layer 2b may be a wedge-shaped convex surface.

Figure 8:
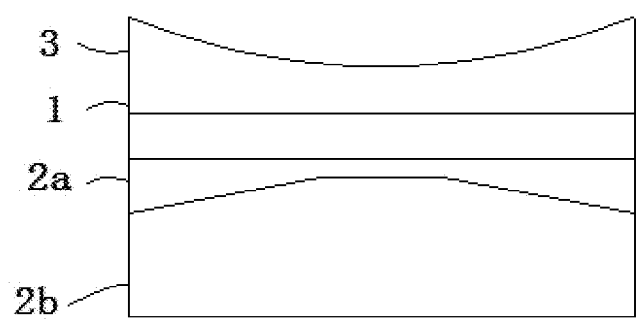
FIG. 8 schematically shows one embodiment of the ultrasonic transducer.

In FIG. 8, an ultrasonic transducer is shown in which the back surface of the high impedance backing layer 2a is a trapezoidal concave surface, and, correspondingly, the front surface of the low impedance backing layer 2b may be a trapezoidal convex surface.

Figure 9:
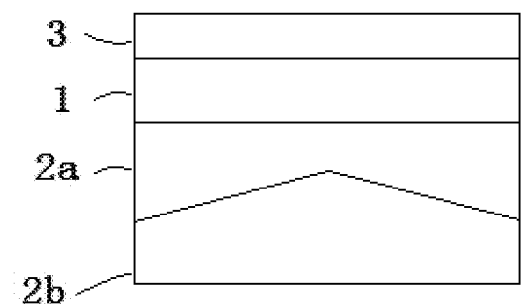
FIG. 9 schematically shows one embodiment of the ultrasonic transducer.

In FIG. 9, an ultrasonic transducer is illustrated in which the matching layer 3 may have a constant thickness, the front surface and back surface of the matching layer 3 may both be flat surface, the back surface of the high impedance backing layer 2a may be a wedge-shaped concave surface, the wedge tip of the wedge-shaped concave surface may point to the piezoelectric crystal, and, correspondingly, the front surface of the low impedance backing layer 2b may be a wedge-shaped convex surface.

Figure 10:
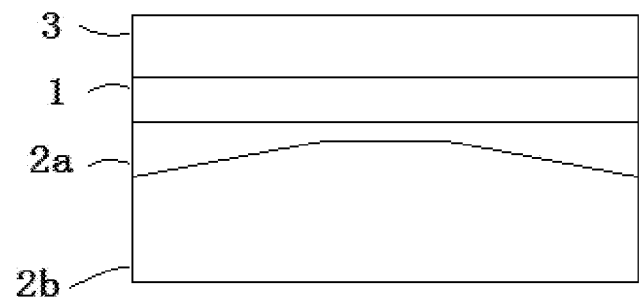
FIG. 10 schematically shows one embodiment of the ultrasonic transducer.

FIG. 10 shows an embodiment of the ultrasonic transducer in which the matching layer 3 may have a constant thickness, the front surface and back surface of the matching layer 3 may both be flat surface, the back surface of the high impedance backing layer 2a may be a trapezoidal concave surface, and, correspondingly, the front surface of the low impedance backing layer 2b may be a trapezoidal convex surface.

Figure 11:
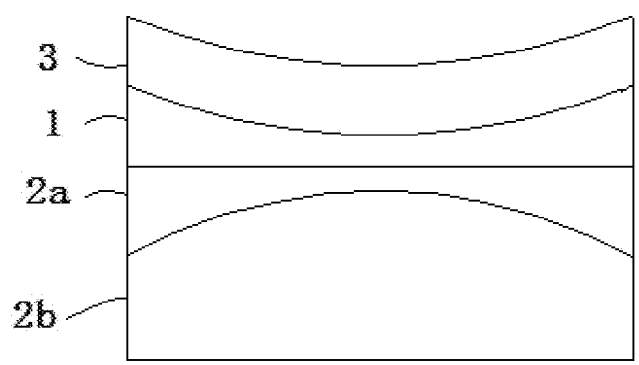
FIG. 11 schematically shows one embodiment of the ultrasonic transducer.

As shown in FIG. 11, an ultrasonic transducer may include a matching layer 3, a piezoelectric crystal 1, a high impedance backing layer 2a, and a low impedance backing layer 2b, which are sequentially stacked from top to bottom. The matching layer 3 may have a constant thickness. The front surface of the matching layer 3 may be a curved concave surface and the back surface may be a curved convex surface. The piezoelectric crystal 1 may have non-constant thicknesses, and the thickness at the middle of the piezoelectric crystal 1 may be smaller than those at both sides. The front surface of the piezoelectric crystal 1 may be a curved concave surface and the back surface of the piezoelectric crystal 1 may be a flat surface. The high impedance backing layer 2a may have non-constant thicknesses, and the thickness at the middle of the high impedance backing layer 2a may be smaller than those at both sides. The front surface of the high impedance backing layer 2a may be a flat surface and the back surface of the high impedance backing layer 2a may be a curved concave surface. The low impedance backing layer 2b may have non-constant thicknesses, and the thickness at the middle of the low impedance backing layer 2b may be larger than those at both sides. The front surface of the low impedance backing layer 2b may be a curved convex surface.

Figure 12:
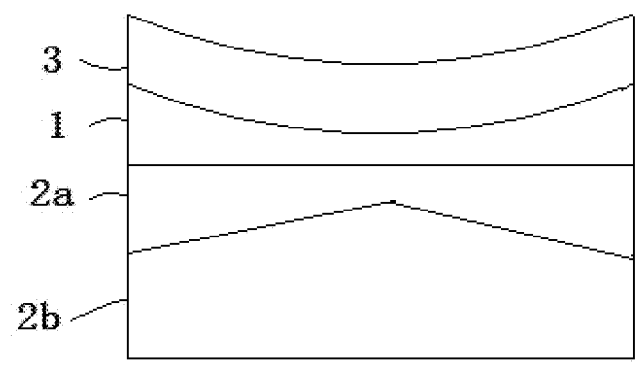
FIG. 12 schematically shows one embodiment of the ultrasonic transducer.

In FIG. 12, an ultrasonic transducer is shown in which the back surface of the high impedance backing layer 2a may be a wedge-shaped concave surface and the wedge tip of the wedge-shaped concave surface may point to the piezoelectric crystal.

Figure 13:
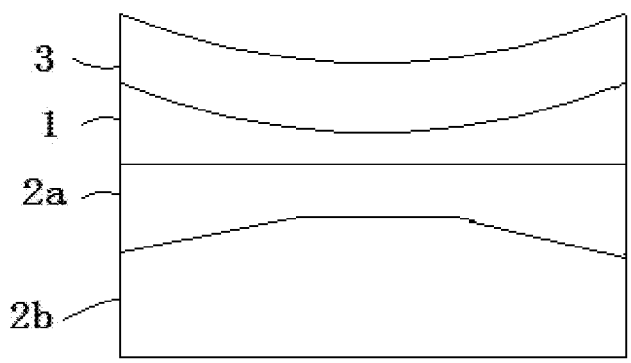
FIG. 13 schematically shows one embodiment of the ultrasonic transducer.

In FIG. 13, an ultrasonic transducer is shown in which the back surface of the high impedance backing layer 2a may be a trapezoidal concave surface and correspondingly the front surface of the low impedance backing layer 2b may be a trapezoidal convex surface.

The ultrasonic transducer may include the matching layer, the piezoelectric crystal, the high impedance backing layer and the low impedance backing layer. The matching layer can achieve the impedance matching between human tissue and the piezoelectric crystal. The piezoelectric crystal may be an element with piezoelectric effect. Both of the high impedance backing layer and the low impedance backing layer can absorb sound waves and achieve damping effect, and can increase the bandwidth of the ultrasonic transducer. The larger the impedance, the larger the damping effect will be, and the wider the bandwidth. The matching layer may have a constant thickness or non-constant thicknesses. The piezoelectric crystal may be connected with the high impedance backing layer to form an equivalent piezoelectric crystal which may have non-constant thicknesses. The thickness at the middle of the equivalent piezoelectric crystal may be smaller than those at both sides thereof. The low impedance backing layer may have non-constant thicknesses. The thickness at the middle of the low impedance backing layer may be larger than those at both sides thereof.

The acoustic impedance of the high impedance backing layer may be larger than that of the piezoelectric crystal. The acoustic impedance of the low impedance backing layer may be smaller than that of the piezoelectric crystal. In order to increase the sensitivity of the ultrasonic transducer, the difference between the high and low acoustic impedance may be appropriately increased. For example, the acoustic impedance of the high impedance backing layer may be n times of the acoustic impedance of the piezoelectric crystal, and the acoustic impedance of the piezoelectric crystal may be m times of the acoustic impedance of the low impedance backing layer. Herein n and m may both be greater than 1. In one embodiment, the acoustic impedance of the high impedance backing layer may be 3 times of the acoustic impedance of the piezoelectric crystal, and the acoustic impedance of the low impedance backing layer may be $\frac{1}{10}$ of the acoustic impedance of the piezoelectric crystal. The sound waves propagating backwards from the piezoelectric crystal may mostly enter into the high impedance backing layer and then be strongly reflected at the interface between the high impedance backing layer and the low impedance backing layer. Accordingly, almost all of the sound waves may be reflected back to the piezoelectric crystal, which can greatly increase the sensitivity of the ultrasonic transducer.

In the ultrasonic transducer, the interface between the high impedance backing layer and the low impedance backing layer may have a relatively large reflection coefficient and can generate strong reflected waves, such that the high impedance backing layer with non-constant thicknesses and the piezoelectric crystal with constant thickness can equivalently replace the piezoelectric crystal with non-constant thicknesses, thereby greatly reducing the difficulty in manufacturing the piezoelectric crystal. Furthermore, since the fragile piezoelectric crystal has constant thickness, the ordinary process can guarantee the safety of the crystal. In addition, because the ratio of the maximum thickness and the minimum thickness (maximum thickness/minimum thickness) of the high impedance backing layer with non-constant thicknesses can be relatively large, i.e., the ratio of the maximum thickness and the minimum thickness (maximum thickness/minimum thickness) of the equivalent piezoelectric crystal can be larger, such as the ratio can be greater than or equal to 200%, the bandwidth of the ultrasonic transducer can be wider. By adjusting the maximum thickness of the high impedance backing layer, the low frequency band of the ultrasonic transducer can be adjusted. By adjusting the minimum thickness of the high impedance backing layer, the high frequency band of the ultrasonic transducer can be adjusted.

The present disclosure has been described in detail above with reference to the specific embodiments. However, it shall not be interpreted as that the specific implementations of the present disclosure are limited thereto. For a person ordinarily skilled in the art, many simple deductions or alternatives can be made without departing from the concepts of the present disclosure.

The invention claimed is:

1. An ultrasonic transducer, comprising a matching layer, a piezoelectric crystal and a backing layer, wherein a back surface of the matching layer is connected with a front surface of the piezoelectric crystal, the backing layer comprises a high impedance backing layer and a low impedance backing layer, a back surface of the piezoelectric crystal is connected with a front surface of the high impedance backing layer, and a back surface of the high impedance backing layer is connected with a front surface of the low impedance backing layer, and wherein the high impedance backing layer has non-constant thicknesses;
wherein the piezoelectric crystal has a constant thickness, and both the front surface and the back surface of the piezoelectric crystal are flat surfaces;
the matching layer has non-constant thicknesses, wherein the back surface of the matching layer is a flat surface, and a front surface of the matching layer is a curved concave surface.

2. The ultrasonic transducer of claim 1, wherein a thickness at a middle of the high impedance backing layer is smaller than thicknesses at both sides of the high impedance backing layer.

3. The ultrasonic transducer of claim 2, wherein the back surface of the high impedance backing layer is a curved concave surface or a trapezoidal concave surface.

4. The ultrasonic transducer of claim 2, wherein the front surface of the high impedance backing layer is a flat surface.

5. The ultrasonic transducer of claim 2, wherein the back surface of the high impedance backing layer is a wedge-shaped concave surface.

6. The ultrasonic transducer of claim 1, wherein, a thickness at middle of the high impedance backing layer is smaller than thicknesses at both sides of the high impedance backing layer and the back surface of the high impedance backing layer is a concave surface, a thickness at middle of the low impedance backing layer is larger than thicknesses at both sides of the low impedance backing layer and the front surface of the low impedance backing layer is a convex surface, and the back surface of the high impedance backing layer matches with the front surface of the low impedance backing layer.

7. The ultrasonic transducer of claim 1, wherein the matching layer has non-constant thicknesses, and a thickness at middle of the matching layer is smaller than thicknesses at both sides of the matching layer.

8. An ultrasonic diagnostic device, comprising an ultrasonic transducer of claim 1.

9. An ultrasonic transducer, comprising a piezoelectric crystal and a backing layer, wherein the backing layer comprises a high impedance backing layer and a low impedance backing layer, a back surface of the piezoelectric crystal is connected with a front surface of the high impedance backing layer, and a back surface of the high impedance backing layer is connected with a front surface of the low impedance backing layer, and wherein the high impedance backing layer has non-constant thicknesses;
wherein the piezoelectric crystal is used for generating ultrasonic waves; a portion of the ultrasonic waves are transmitted to the backing layer, and said portion of the ultrasonic waves transmitted to the backing layer are reflected back towards the piezoelectric crystal by an interface between the high impedance backing layer and the low impedance backing layer; and
wherein the piezoelectric crystal has a constant thickness, the high impedance backing layer has a minimum thickness at its center and a maximum thickness at its side, wherein a ratio between (the maximum thickness+ the constant thickness) and (the minimum thickness+ the constant thickness) is at least 200%.

10. The ultrasonic transducer of claim 9, wherein a thickness at a middle of the high impedance backing layer is smaller than thicknesses at both sides of the high impedance backing layer.

11. The ultrasonic transducer of claim 10, wherein the back surface of the high impedance backing layer is a wedge-shaped concave surface.

12. The ultrasonic transducer of claim 9, wherein a thickness at middle of the high impedance backing layer is smaller than thicknesses at both sides of the high impedance backing layer and the back surface of the high impedance backing layer is a concave surface, a thickness at middle of the low impedance backing layer is larger than thicknesses at both sides of the low impedance backing layer and the front surface of the low impedance backing layer is a convex surface, and the back surface of the high impedance backing layer matches with the front surface of the low impedance backing layer.

13. The ultrasonic transducer of claim 9, further comprising a matching layer, wherein a back surface of the matching layer is connected with a front surface of the piezoelectric crystal.

14. The ultrasonic transducer of claim 13, wherein, the matching layer has non-constant thicknesses, and a thickness at middle of the matching layer is smaller than thicknesses at both sides of the matching layer.

15. An ultrasonic transducer comprising a piezoelectric crystal and a backing layer, wherein the backing layer comprises a high impedance backing layer and a low impedance backing layer, a back surface of the piezoelectric crystal is connected with a front surface of the high impedance backing layer, and a back surface of the high impedance backing layer is connected with a front surface of the low impedance backing layer, and wherein the high impedance backing layer has non-constant thicknesses;

wherein an acoustic impedance of the high impedance backing layer is at least 30 times of an acoustic impedance of the low impedance backing layer; and wherein the piezoelectric crystal is configured for generating ultrasonic waves; a portion of the ultrasonic waves are transmitted to the backing layer, and said portion of the ultrasonic waves transmitted to the backing layer are reflected back towards the piezoelectric crystal by an interface between the high impedance backing layer and the low impedance backing layer.

16. The ultrasonic transducer of claim 15, wherein both the piezoelectric crystal and the high impedance backing layer have non-constant thickness.

17. The ultrasonic transducer of claim 16, wherein a thickness at middle of the piezoelectric crystal is smaller than thicknesses at both sides of the piezoelectric crystal, and a thickness at middle of the high impedance backing layer is smaller than thicknesses at both sides of the high impedance backing layer.

18. The ultrasonic transducer of claim 17, wherein a front surface of the piezoelectric crystal is a concave surface, the back surface of the piezoelectric crystal is a flat surface, the front surface of the high impedance backing layer is a flat surface, and the back surface of the high impedance backing layer is a curved concave surface, a wedge-shaped concave surface or a trapezoidal concave surface.

* * * * *